United States Patent [19]

Allison et al.

[11] Patent Number: 4,460,368
[45] Date of Patent: Jul. 17, 1984

[54] TRANS-DERMAL MEDICATION SYSTEM

[75] Inventors: Kenneth C. Allison, Crystal Lake; Roger D. Allison, Bensenville; Charlotte C. Allison, Crystal Lake, all of Ill.

[73] Assignee: Almedco, Inc., Crystal Lake, Ill.

[21] Appl. No.: 459,499

[22] Filed: Jan. 20, 1983

Related U.S. Application Data

[63] Continuation-in-part of Ser. No. 316,347, Oct. 29, 1981, abandoned.

[51] Int. Cl.$^3$ ................................................. A61M 7/00
[52] U.S. Cl. ..................................... 604/896; 604/897
[58] Field of Search .............................. 604/890–897; 128/130–132, 155, 156; 424/16–26

[56] References Cited

U.S. PATENT DOCUMENTS

| 3,367,332 | 2/1968 | Groves | 128/268 |
|---|---|---|---|
| 3,550,589 | 12/1970 | Wallerstein | 128/156 |
| 3,742,951 | 7/1973 | Zaffaroni | 128/268 |
| 3,972,995 | 8/1976 | Tsuk et al. | 424/28 |
| 3,996,934 | 12/1976 | Zaffaroni et al. | 128/268 |
| 4,055,672 | 10/1977 | Hirsch et al. | 426/127 |
| 4,117,842 | 10/1978 | Hutchins | 128/163 |
| 4,286,592 | 9/1981 | Chandrasekaran | 128/156 |
| 4,297,995 | 11/1981 | Golub | 128/156 |
| 4,309,996 | 1/1982 | Theeuwes | 128/260 |

Primary Examiner—Benjamin R. Padgett
Assistant Examiner—T. J. Wallen
Attorney, Agent, or Firm—Jacque L. Meister

[57] ABSTRACT

A medication application system comprising a container for medication adhesively secured to the unbroken skin of a patient. The container is cup-shaped and closed on its open side by a micro-porous diaphragm or membrane through which the medication passes from the container to the skin surface where it is absorbed. Particular means are described for adhering the container to the skin and for sealing the container prior to its use. Various pharmaceutically effective medications in differing concentrations found to be effectively dispensed from the container, are described.

31 Claims, 9 Drawing Figures

TRANS-DERMAL MEDICATION SYSTEM

BACKGROUND OF THE INVENTION

This invention is a continuation-in-part of application Ser. No. 316,347, filed Oct. 29, 1981, for an improved trans-dermal medication application cell, now abandoned.

This invention relates generally to medication application systems and more particularly to medications and their containers adapted to dispense the medication contained in their interior through a micro-porous film to and through the skin of the patient. This type of medication application system is sometimes characterized as a "trans-dermal application system".

Trans-dermal applications of medication are well known. In particular, Chandrasekaran in Pat. No. 4,201,211 describes a skin patch for delivering medication to the patient's skin where it is absorbed at a controlled rate which depends principally on the medication's concentration and the micro-porous membrane in its area which is in contact with skin. Another similar device has been disclosed by Alejandro Zaffaroni in U.S. Pat. Nos. 3,996,934 and 3,742,951 both of which disclose "bandage type" applications. In such applications, the medication is dispersed in a carrier layer which alone or with a metering layer of microporous film, establishes medication flow rate to the skin. Because of the need for dispersion, the medication necessarily must be non-reactive with the carrier layer material and hence, requires different materials for the construction of the reservoir layer depending on the medication.

This required non-uniformity in construction has as a concomittant requirement that the applicator be fabricated with the medication in place and this, in turn, causes problems with diminishing shelf-life of the package since the medication is subject to deterioration as soon as the applicator is fabricated. Additionally, there are medications for which it is difficult or impossible to find a long-lived compatible dispersing material. Further, the complete package is inherently fragile because of the fragile nature of the reservoir layer.

In still other bandage type applicators, the medication material is carried as a gelatinous material in a reservoir. While it would appear that this type of construction would overcome the limitations of the above-described bandage type applicators, those heretofore known have been difficult to fill and often subject to considerable lateral medication leakage with frequent secondary problems of staining of clothing or skin.

In the practice of the invention, systemically active drugs are used to fill the inventive medication container. These drugs are ones which, when applied to the skin, are absorbed through the body surface to which applied and are then dispersed in the body tissue by the patient's various circulatory systems.

The systemically active drugs employed in the practice of the invention are ones which are conventionally administered either orally or by injection with the object being to disperse the medication in the tissue to be treated at a controlled rate.

However, the oral or injection ingestion methods have certain well-known disadvantages as pointed out in the prior art, principal of those being maintenance of asepsis with respect to injection and the need to disperse the drugs throughout the circulatory system for oral administration where topical ministration may be desired. To avoid the problems of the oral or injection methods of application or still other methods of application well-known in the art, it has been found that systemically active drugs can be administered trans-dermally through the unpunctured skin. Since with trans-dermal application a drug can be administered in a localized area that it is desired to treat, and, since the skin layer is not broken, asepsis is not ordinarily a problem and many of the other difficulties of the prior art, including pain during administration, are overcome by the trans-dermal application method of the invention.

SUMMARY OF THE INVENTION

A principal object of the invention is to provide a new and improved medication application system that overcomes the foregoing recited and other limitations of the prior art.

Still another object of the invention is to provide a medication system having a new and improved medication container that is readily fillable with a wide variety of medications at high production rates.

Yet another object of the invention is to provide a medication administration system having a new and improved medication container capable of separately holding plural medication compositions for simultaneous application at the same or dissimilar rates.

Another object of the invention is to provide in a medication administration system a new and improved medication container bar and color or otherwise codable to indicate the medication contents.

A further object of the invention is to provide in a medication administration system a new and improved medication container that is capable of being filled by the prescriber or pharmacist supplier of the patient.

A still further object of the invention is to provide in a medication administration system a new and improved medication container more comfortable in use than any heretofore known.

The foregoing and other objects of the invention are achieved in the preferred embodiment of the system of the invention through use of a medication container closed on its skin contacting side by a micro-porous diaphragm the whole of which is surrounded by an annular, perforated foam, skin mounting medium. A release sheet and an impermeable seal protect the contents of the medication container from contamination or leakage until the time of application. The container is filled with a systemically active medication and the container sealed until made ready for use. The nature of the invention and its several features and objects will appear more fully from the following description made in connection with the accompanying drawings.

DESCRIPTION OF THE PREFERRED EMBODIMENTS

Figure 1:
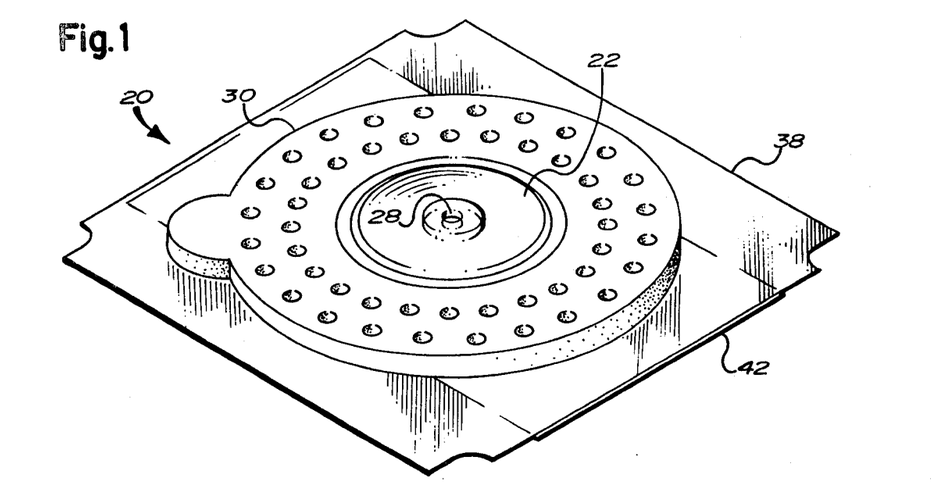
FIG. 1 is a perspective view of the medication container of the invention.
Figure 2:
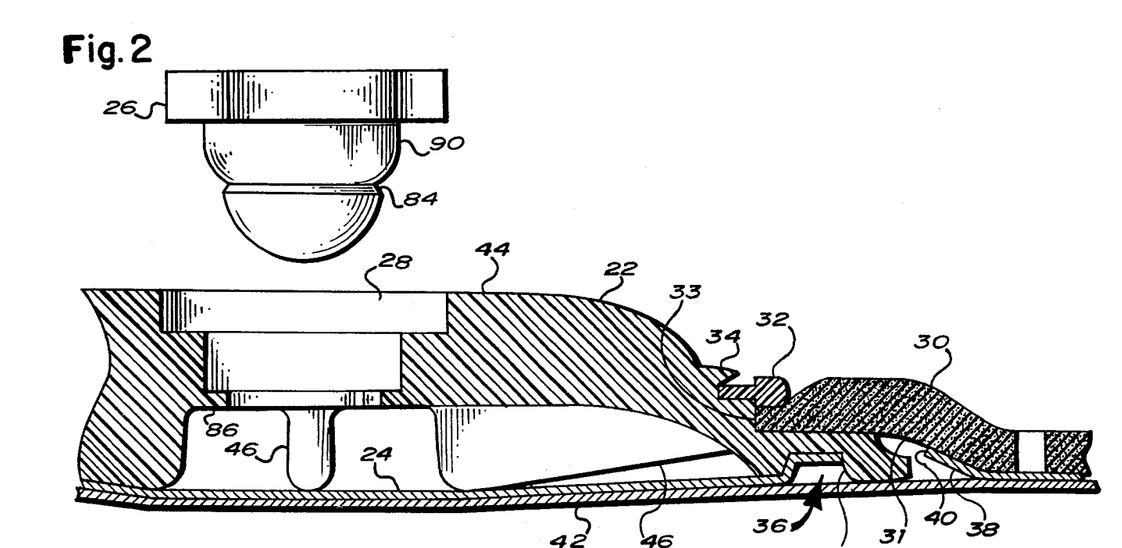
FIG. 2 is an enlarged view in cross-section of the medication container of the invention with portions broken away.
Figure 3:
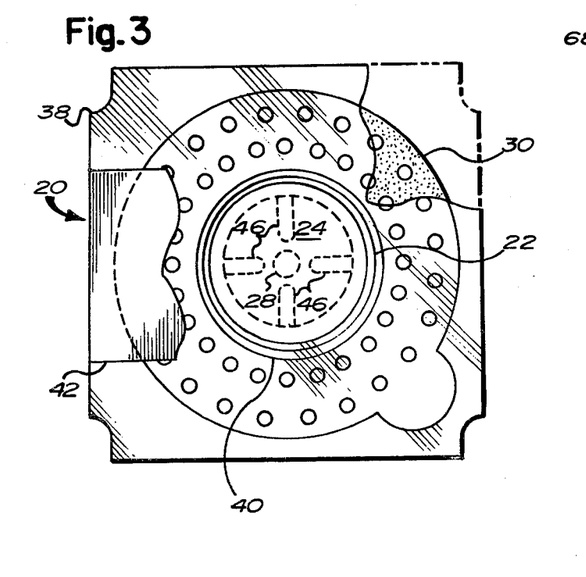
FIG. 3 is a bottom view of the medication container of FIG. 1 with portions of the release sheet and foil seal partially broken away to show details thereof.

FIGS. 1-3 illustrate the principal embodiment of the invention. In FIGS. 1 and 3 there are shown top and bottom views of the complete medication container at 20 with FIG. 2 being a cross-section thereof. A generally concave shaped housing 22 having an outwardly extending flange 23 at its periphery is closed on its open side by a micro-porous diaphragm or membrane 24 to form the medication container. The micro-porous membrane is advantageously secured to housing 22 as by heat sealing in the area of the annular depression 36 in the flange 23 near the edge of the housing. Because of this depressed location of the sealed edge, the somewhat rough edges of membrane 24 which might other wise irritate a patient's skin are prevented from coming into skin contact when the container is in use applied to the skin of a patient/user.

A retaining plug 26 inserted in housing 22 is used to close and seal the filling aperture 28 in the housing after filling of the housing with a selected medication. A skin-adhering medical foam tape 30 is adhesively secured to flange 23 of housing 22 and mechanically secured thereto by retaining ring 32 which is, in turn, secured to housing 22 by hot staking at 34. Tape 30 is coated with medical adhesive 31 over its entire lower skin-contacting surface to achieve its skin-adhering qualities. A release sheet 38 is sealed to the foam tape by the same adhesive 31 that is used to adhere the foam tape to the skin of a patient. The release sheet prevents exposure of that adhesive before it is adhered to the skin. Advantageously, the release sheet 38 is coated with an adhesive release agent on the side toward the medical foams adhesive coating to reduce the tightness of the bond therebetween. The foam tape 30 has a central aperture 33. For manufacturing purposes since the foam tape 30 and release sheet 38 are advantageously fastened together before forming to the shapes shown, a central aperture 40 is formed in release sheet 38 at the same time aperture 33 is formed to permit direct contact of the micro-porous film with the patient's skin. The cell assembly is completed by a vapor barrier which advantageously is a 0.002 inch thick aluminum foil strip 42 having a commercial heat seal coating on one side which is heat sealed to the release sheet to block exterior access to the micro-porous membrane. This construction makes the complete cell airtight and, by preventing air or any other non-sterile material from contacting the micro-porous membrane and through it, the medication, thus preserves the medication in a sterile condition over a long shelf life.

The housing 22 is made relatively thick, on the order of between 0.040 inches and 0.100 inches with a median of 0.060 inches. This contrasts with an average thickness of 0.020 inches in other similar prior art type applicators and this, in combination with the foil vapor barrier sealing strip 42, inhibits vapor transmission from the completed medication container. As a result it is not unusual to achieve a 3-year minimum shelf-life for the medication filled container of the invention whereas, prior art devices typically have a shelf-life of less than one year unless they are preserved in a separate sealed container.

Figure 9:
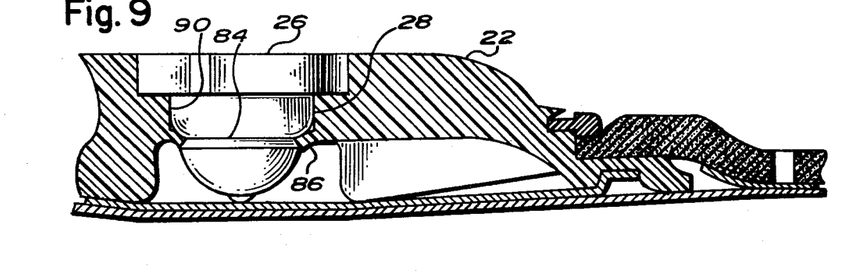
FIG. 9 is a view, similar to that of FIG. 2, showing the 30 medication container with the retaining plug positioned locked in place and sealing the filling aperture.

As described above, retaining plug 26 is used to seal the filling aperture. Advantageously, plug 26 is of the same type described in the patent of Kenneth C. Allison and William H. Cooley, which issued Oct. 5, 1982 as U.S. Pat. No. 4,352,589, for a Blind Riveting and Sealing System. As there described and as shown in FIG. 9, rivet 26 is uniquely configured in combination with housing 22 and its filling aperture 28 to effect a tight seal and by flexing locking flange 86 into beveled locking groove 84, lock itself in position. As explained in the aforesaid patent, the sealing action occurs both under the head 88 of plug 26 and also in the plug shank area of forcefit immediately under the head where it engages housing aperture 28. Further the plug 26 and filling aperture 28 are reciprocally configured so that the top surface 44 of the housing 22 is smooth with the plug in place. The housing 22 is advantageously constructed by molding from radiation resistant clear polypropylene which material is substantially chemically inert in the presence of most medication solutions.

It is a feature of the invention that the interior of housing 22 contains plural identical reinforcing ribs 46. These ribs depend generally away from the interior surface of the housing 22 and assist in supporting the micro-porous membrane in the open area over which it extends. Because of the tapered shape of the ribs, the formation of air-pockets during filling is inhibited. In one preferred embodiment of the invention, the housing encloses a volume of substantially 2 cubic centimeters and has an open side covered by the micro-porous membrane of substantially 5 square centimeters.

The micro-porous membrane 24 is of a commercially available type and, in the preferred embodiment, is 0.001 inches thick with a pore size of 0.02×0.2 micrometers and having a pore volume of substantially 38%. Pores of this size prevent bacterial transmission either from the interior of the medication container to the skin or from the exterior to the interior of the container. Other membrane thicknesses, pore sizes and pore volumes may be used depending on the composition of the medication it is desired to accommodate.

As shown in FIGS. 1 and 3, the foam tape 30 is constructed with a stripping handle 48 for grasping when pulling off the release sheet 38 together with foil vapor barrier strip 42. Tape 30 in the preferred embodiment is 1/16 inch thick white polyethylene closed cell foam. Because this material will be in contact with the user/patient's skin for at least several hours, a series of holes are cut into foam tape 30 to permit evaporation of moisture from the patient's skin. These apertures are shown as two concentric rings of holes the inner ring of which is at a radius greater than that of flange 23. These holes permit the skin to "breath".

It is a feature of the invention that release sheet 38 be high-density polyethylene 0.005" inches thick. This material has the combined desirable properties of toughness, and its ability to heat seal to the foil vapor barrier. Mylar has also been used for this application but is not preferred even though it is tougher, because of problems in adhering it to other materials.

Figure 8:
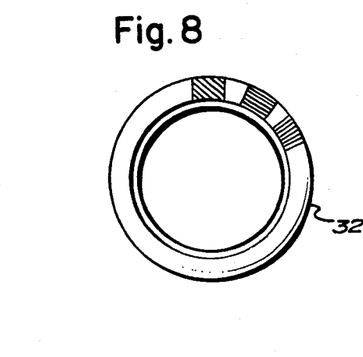
FIG. 8 is a plan view of the annular locking ring employed in the invention showing the use of bar and color coding to identify the contents of the medication container of the invention.

It is a feature of the invention that retaining ring 32 can be bar or color coded and/or otherwise marked to indicate the National Drug Code used by the pharmaceutical industry; such coding and other product or manufacturer designations ordinarily being applied to the filled medication containers to identify the drug in the package and hence lessen the possibility of administering the wrong drug. Here, the retaining ring can be bar color coded or other indicia applied, somewhat in the manner symbolically shown in FIG. 8 and achieve similar results. The marking of ring 32 is especially advantageous since the ring never is in contact with either the user/patient or the medication and hence the marking materials need not be medication compatible or non-allergenic.

Figure 6:
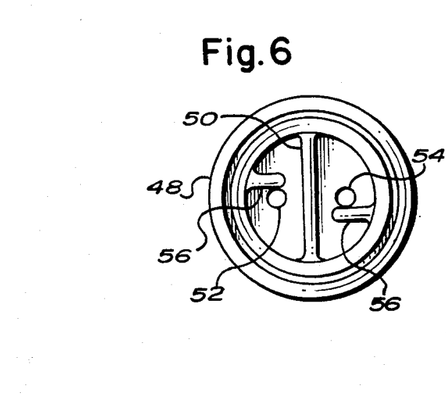
FIG. 6 is a view of a medication container embodiment used for simultaneously dispensing 2 medications.
Figure 7:
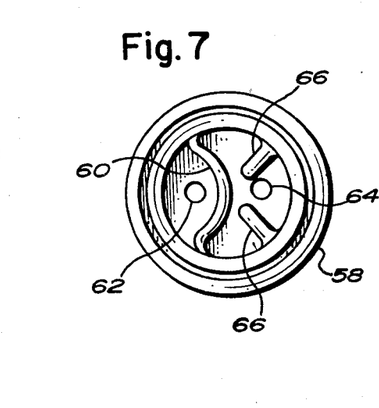
FIG. 7 illustrates an alternative construction of the medication 25 container of FIG. 6.

FIGS. 6 and 7 illustrate alternative configurations of the housing 22 shown in FIGS. 1-4. As best shown in FIGS. 2 and 3, the housing 22 comprises a cup-like single cavity construction. In the FIG. 6 configuration, the basic external shape of the housing 48 is identical to that of FIG. 1 but additionally, a dam 50 is inserted in the interior of the housing cavity dividing the cavity into two compartments having substantially identical volumes. Each of these cavities may be filled with a different medication solution of different concentrations of the same medication, one of which might be a priming dose to rapidly establish a given blood level of medication followed by a sustained administration at a lower concentration. Of course, because of this construction, it is necessary that there be two filling apertures and these are shown at 52 and 54. Because the dam 50 acts as a reinforcing rib, the FIG. 6 configuration has only two reinforcing ribs 56 and, it is frequently possible to eliminate both of these ribs.

The FIG. 7 alternative construction of the housing is similar to that of FIG. 6 in that the housing is divided into two different size compartments. Housing 58 has a dam 60 dividing its interior into two compartments containing substantially ⅓ and ⅔, respectively, of the enclosed volume. Obviously other ratios and additional compartments could be created by relocation of the dam 60 or the addition of further dams. Filling apertures 62 and 64 permit the filling of the two separate compartments and reinforcing ribs 66, where used, function similarly to ribs 46 of FIG. 1. In both the FIGS. 6 and 7 embodiments, a retaining plug such as that shown at 26 in FIG. 2 is used to close and seal the filling aperture after filling.

Figure 4:
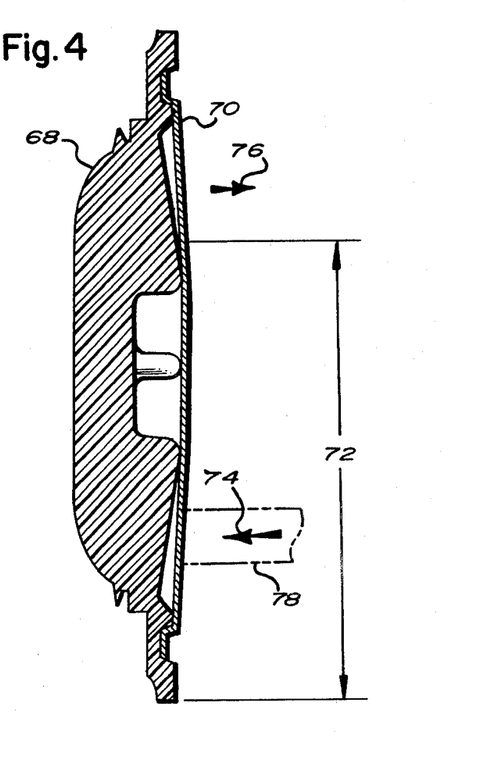
FIG. 4 is a sectional view, partially in phantom, of an alternate construction of the medication container of the invention used in combination with a filling method different from that used with the medication container of FIGS. 1-3.
Figure 5:
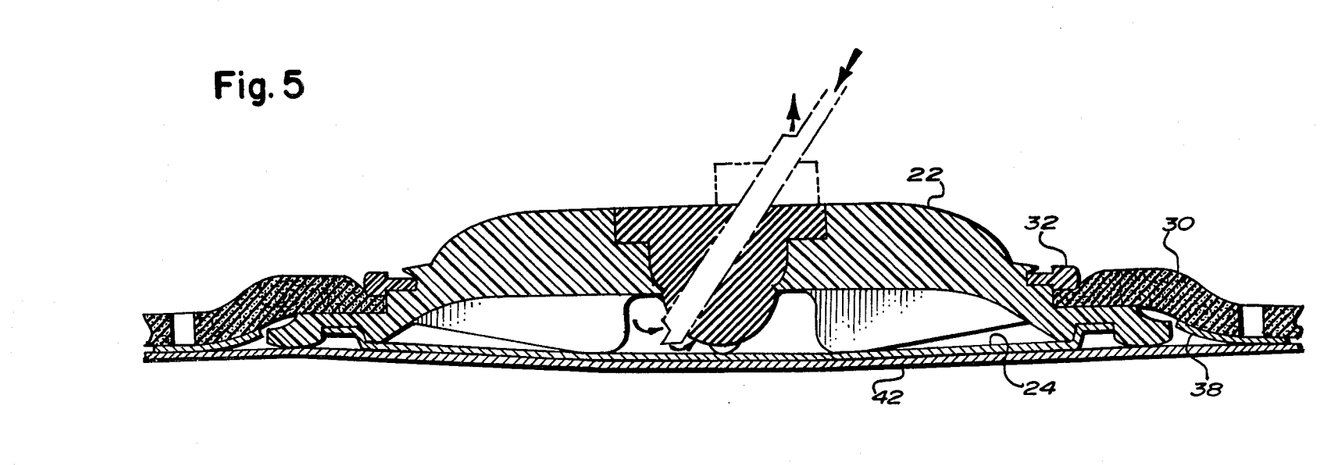
FIG. 5 is a partial section view, partially in phantom, of another alternate construction of the FIGS. 1-3 embodiment used to effect an alternate filling method.

FIGS. 4 and 5 illustrate still further alternative constructions of the medication container of the invention to utilize alternative filling methods. In the FIGS. 1-3 embodiments and in the FIGS. 6 and 7 embodiments, the cell is filled by more or less conventional methods such as might be used to fill any container before a sealing closure is applied. In each of the FIGS. 4 and 5 embodiments, the filling is done in a substantially different manner after the sealing closure is applied.

In FIG. 4, the housing 68 is substantially identical to the housing 22 of FIG. 2 except that it does not contain a filling aperture. As shown, the assembly is readied for filling by heat sealing a micro-porous membrane 70 to the housing in the same manner heretofore described. The membrane 70 is then wetted with an appropriate solution over substantially ¾ of the area which covers the medication cavity as schematically indicated at 72. One appropriate solution because it is both inexpensive and sterile, is isopropyl alcohol. The membrane area that has been wetted is not air permeable except under fairly high pressure whereas the dry membrane is air permeable.

After wetting, a medication filling tube 78 is placed against the membrane in the wetted area and medication under pressure to move in the direction of arrow 74 applied to the exterior of membrane 70. The pressure used, while above atmospheric, is on the order of a few inches of water. Medication then passes through the micro-porous membrane to fill the container. The air inside the container is forced out past the membrane in the direction of arrow 76 by the medication displacing it until the container is full of the medication solution. With only 2-3 inches of water as a working pressure, fill times have been approximately one (1) second.

The FIG. 5 embodiment is substantially identical to that of FIG. 2 except that the filling aperture is filled with a molded in place medical grade soft rubber plug 80 in place of the plug 26. Then, filling is accomplished by means of a double hollow needle filling tool 82, one of which inserts the medication into the cell, the other permitting the escape of trapped interior air. When the tool 82 is withdrawn after filling, the plug 80 self-seals.

The foregoing has described the basic medication container and its several preferred embodiments. These embodiments can be used with a variety of medications since the materials of the inventive medication container do not react with the great majority of medications that might be placed therein. Virtually any drug with an ionic charge which is soluble in water and which can pass through the membrane could be introduced locally. The major medication categories that have been investigated thus far and which appear to be of primary interest would be anti-inflammatory and painkilling drugs including Acetyl salicylic acid (aspirin), Glucocortcoids (hydrocortisone and cortisone) and their synthetic analogs such as Dexamethasone and its components, Acetaminophen and Sulindac (clinoril). Additionally, coronary vasodilators such as Glyceryl trinitrate (nitro-glycerine) for the relief of angina pectoris, general cardiac stimulators such as the Digitalis glucosides, antiarrhythmics such as Quinidine and antidiabetic agents such as Insulin have been investigated with favorable preliminary results for trans-dermal ministrations. These medications are all ordinarily placed in a physiologically neutral or slightly stronger aqueous saline (NaCl) solution on the order of 0.9% to 15%, 0.9% being essentially the normal salinity of the human body. It has been found that as the salinity of the solution containing the medication is increased, body fluids are increasingly attracted to the medication container interior where they displace the containers medication containing contents; the displaced contents containing the medication then migrating through the microporous membrane to the skin surface where they may be absorbed. The higher the medication solution salinity, the greater the transfer rate from the body to the container. If the salinity is less than 0.9%, the body attracts the fluid in the container which then empties without refilling. Bacterial inhibitors may also be added depending on the active medication employed and it has been found advantageous to employ wetting agents to enhance the initial transfer rate; polyoxyethylene (commercially known as Polysorbate 80) having proved especially useful. By the addition of Glycerin to the mixture in the medication container, freezing of the container contents may be alleviated, a 50% Glycerine solution having a freezing point of −20° F.

EXAMPLE NO. 1

One medication-solution combination that has proven especially effective as an analgesic and anti-inflammatory agent when placed in the inventive medication container, employs Aspirin (Acetyl salicylic acid) in a 3½% aqueous saline solution with one-half percent of Polysorbate 80 (wetting agent). The Aspirin is placed in the solution in a concentration of between 0.15% and 2%, the solution being capable of absorbing about 0.25% Aspirin (0.136% by weight) and the excess, if any, remaining undissolved in the container. With only saturated solutions and no undissolved Aspirin, the contents of the container are completely absorbed through the skin in about 24 hours.

EXAMPLE NO. 2

In another series of tests, Aspirin was mixed with a 3½% NaCl solution containing 0.1% Polysorbate 80 (Polyoxylethylene) in a concentration of 136.3 mg per 100 ml and the containers applied to the external epiderma of an arthritic knee. After 24 hours, on average, 57.5 mg of Aspirin per 100 ml had been absorbed with substantial reduction in pain and inflammation commencing after about 3 hours and containing for several hours (up to 6) after removal of the container from the knee.

EXAMPLE NO. 3

Another formulation useful for painkilling, employs Acetaminophen in a solution concentration of between 0.05% to 20% with the preferred solution concentrations being between 0.4% and 2%. The 0.05% concentration appeared to be a bottom threshold below which no effect could be noticed and the 20% concentration, the maximum that could be transferred under ideal conditions before removal of the container. In an aqueous saline (NaCl) solution of between 0.02% and 3½% containing Polysorbate 80 as a wetting agent in a concentration of 0.1% and Glycerol between 0% and 50%, successful transfers of the entire medication contents of the container exclusive of glycerol to the patient took place over a period of between 24 hours and 3 days depending on the concentrations involved and the components of carrier solutions.

EXAMPLE NO. 4

Another painkilling, anti-inflammatory formulation usefully employed in the inventive medication container comprises Aspirin between 0.5% to 10% with a preferred range of 0.1% to 2%, Acetaminophen between 0.05% and 10% with a preferred range of 0.1% to 2% in a Sodium Cloride aqueous solution between 0.02% and 20% with a preferred range of 0.2% to 3.5%, with a wetting agent Polyoxyethylene between 0.01% and 0.5% and with or without Glycerol to inhibit freezing. Pharmacologically and subjectively, the painkilling, anti-inflammatory properties prove to be substantially the same as either of the first two examples.

EXAMPLE NO. 5

Sulindac is also an anti-inflammatory agent but, of considerably greater potency than Aspirin or Acetaminophen. When dissolved in an aqueous saline (NaCl) solution of between 0.02% and 20% (preferred 0.2% to 3.5%) in a concentration between 0.01% and 0.20% with a preferred range of 0.02% to 0.1%, favorable results were achieved similar to that described above in Examples 2 and 3, and without the side effects common with oral ingestion.

EXAMPLE NO. 6

As noted above, nitro-glycerine may advantageously be administered over a considerable time period to provide relief from the pains of angina pectoris. In a 3½% aqueous saline solution (Sodium Chloride) it has proven advantageous to place between 12.5 mg and 37.5 mg/ml to achieve daily ministration levels between approximately 5.25 mg and 15.75 mg, respectively.

EXAMPLE NO. 7

Digitalis glycosides may be administered over a sustained period trans-dermally to achieve good control, especially with patients who otherwise are careless in taking medications. 0.5 mg of digitalis is placed in 2 cc of a solution containing 40% propylene glycol, 10% alcohol and water to achieve a daily ministration rate of 0.25 mg.

EXAMPLE NO. 8

Insulin is capable of being administered trans-dermally when dissolved in saline solutions. It has been found that 40 units placed in suspension in a 3% aqueous saline solution with about 1.6% glycerine in the 2 CC volume of the inventive container transfers approximately 16–22 units per day.

EXAMPLE NO. 9

The glucocorticoids such as hydrocortisone and its synthetic analogos such as dexamethazone are readily absorbed through the skin and are of particular advantage in that application for the palliative treatment of chronic rheumatoid arthritis and other inflammatory ailments. Hydrocortisone in a concentration of 4 mg/ml in an aqueous 3½% sodium chloride solution containing polysorbate 80 and methyl paraben, 0.18% as a preservative is absorbed at the rate of between 1.7 and 2 mg per day of the hydrocortisone. Similar results are achieved with similar concentrations of dexamethazone sodium phosphate solution.

EXAMPLE NO. 10

Quinidine is used in the treatment of arrhythmias, atrial fibrillation and ventribular tachycardia, among others. When quinidine gluconate is employed in a concentration of 50 mg/ml in a sterile water solution, about 22 mg/ml are absorbed daily from the inventive device.

The foregoing description of transfer rates from the medication container to the epiderma of a patient have been established by experimental observation. However, there are many theoretical means of determining the permeability of the microporous diaphragm or membrane including those based upon the use of Ficks laws of diffusion. Each of these, ultimately, results in a permeability constant which is an inherent characteristic of the material comprising any given medication compound and micro-porous diaphragm. The embodiments of the medication container described may be used to effect these transfers and, of course, the embodiments of FIGS. 6 and 7 to effect two different rates of ministration.

As pointed out above an important feature of the invention is the discovery that varying strengths of saline solutions in transdermal containers effects the direction of flow, to or from the container, and the medication transfer rate and its duration. When saline solutions are employed as a medication carrier in the container of the invention, the salinity of the solution in the container taken in combination with the normal body salinity of the user/patient results in a force driving container contents either into or out of the medication container. This driving force must be accounted for in determining the permeability constant of the container and medication contents. As has been pointed out, sub-normal salinity (less than 0.9%) results in medication migration to the user/patient (termed negative driving force) whereas salinity in excess of 0.9% results in body fluid migration into the container (termed positive driving force).

For a negative driving force solution, the container is emptied, the body attracting the container contents. For a positive driving force solution, body fluids are attracted to the container which then continuously refills until it reaches normal body salinity.

An understanding of these driving forces, negative or positive, is helpful in determining quantitative container medication contents for any particular medication. Where it is desired that only a fixed amount of medication be applied over a short time span, negative driving force solutions are preferred because the entire container contents will be dispensed in one or 2 days. For longer term applications positive driving force solutions are advantageous and preferred since they offer the feature of relatively high initial dosages with a tapering effect reducing the rate of ministration of the medication as the body fluid transported into the container continuously dilutes the medication contents. Of course, for certain medications such as aspirin, the positive driving force solutions offer still another advantage. Since only a fixed amount of aspirin will go into solution and thus be capable of transport to the skin surface, if additional aspirin beyond the saturation level is placed in the container, the undissolved material will go into solution as the body fluids replace the original container contents. This then offers a means for prolonging the effect of the aspirin (and similarly soluble materials) at saturation levels for many days.

The invention has been described in detail herein with particular reference to preferred embodiments thereof. However, while each of these embodiments are described, it will be understood that variations and modifications can be effected within the spirit and scope of the invention described hereinabove and as defined in the appended claims:

What is claimed is:

1. A medication application system for the sustained administration of acetyl salicylic acid transdermally through an area of unbroken skin, comprising
    a medication container including medication impermeable housing means forming a generally concave shaped cavity open on one side and having flange means extending radially outward from the periphery of said cavity opening and integral with said housing means, said flange means having an annular depression therein on the side of said flange means nearest said concave cavity opening,
    medication permeable micro-porous membrane means secured in said annular depression of said flange means of said housing means and covering the open side thereof to thereby form a medication holding container permeable on one side only to the passage of medication, means secured to said housing for adhering said medication holding container to the skin of a patient, and
    acetyl salicylic acid in an aqueous saline solution providing a positive driving force in said medication holding container, said acetyl salicylic acid being in a concentration to provide a sustained analgesic and anti-inflammatory action.

2. A medication application system for the sustained administration of acetyl salicylic acid transdermally through an area of unbroken skin, comprising
    a medication container including medication impermeable housing means forming a generally concave shaped cavity open on one side, said housing means further comprising filling aperture means centrally located in said concave cavity and flange means extending radially outward from the periphery of said cavity opening and integral with said housing means, said flange means having an annular depression therein,
    medication permeable micro-porous membrane means secured in said annular depression and covering the open side of said cavity to thereby form a medication holding container permeable on one side only to the passage of medication,
    means secured to said housing means for adhering said medication holding container to the skin of a patient, and acetyl salicylic acid in an aqueous saline solution in said medication holding container in a concentration to provide a sustained analgesic and anti-inflammatory action.

3. A medication application system in accord with claim 2 further comprising retaining plug means inserted in said filling aperture means to sealingly close said filling aperture.

4. A medication application system in accord with claim 3 wherein said retaining plug means comprises a molded-in-place soft rubber plug.

5. A medication application system in accord with claim 2 wherein said housing means further comprises one or more reinforcing rib means integrally formed withing said housing means and depending therefrom into said cavity for supporting said micro-porous membrane means.

6. A medication application system in accord with claim 2 wherein said skin adhering means further comprises adhesive means for adhesively securing said skin adhering means to both the opposite surface of said flange means from the side with said annular depression and to the skin of a patient.

7. A medication application system in accord with claim 6 further comprising retaining ring means mechanically secured to said housing means to thereby compress and secure said skin adhering means to said flange means, said retaining ring means further comprising coding indicia applied thereto.

8. A medication application system in accord with claim 7 further comprising release sheet means secured to said skin adhering means radially outward from said flange means, said release sheet means having a central aperture therein equal to or larger in diameter than the flange diameter of said housing means and located concentric therewith.

9. A medication application system in accord with claim 8 further comprising vapor barrier means sealingly adhered to said release sheet means and extending over said central aperture of said release sheet means to thereby block exterior access to said micro-porous membrane means.

10. A medication application system in accord with claim 8 wherein said acetyl salicylic acid solution comprises a positive driving force acqueous saline solution with aspirin in a concentration of between 0.15% and 2%.

11. A medication application system for the sustained administration of analgesic and anti-inflammatory agents, transdermally through an area of unbroken skin comprising,
A medication container comprising
medication impermeable housing means forming a generally concave shaped cavity open on one side, flange means extending radially outward from the periphery of said cavity opening including an annular depression therein, filling aperture means centrally located in said concave cavity and reinforcing rib means integrally formed within said housing and depending therefrom into said concave cavity,
medication permeable micro-porous membrane means secured to said annular depression and covering the open side of said cavity,
retaining plug means sealingly inserted in said filling aperture means,
skin adhering means having a central aperture whose diameter is substantially equal to that of said cavity opening and concentric therewith, said skin adhering means being secured to said housing's flange means on the side opposite said membrane means and comprising a plurality of holes perforated in said skin adhering means in the area thereof extending radially outward from said housing flange area,
release sheet means having a central aperture equal to or larger in diameter than the inside flange diameter of said housing means and located concentric therewith, said release sheet means being adhesively secured to said skin adhering means,
retaining ring means mechanically secured to said housing means to thereby compress and secure said skin adhering means to said housing flange means,
vapor barrier means sealingly adhered to said release sheet means and extending over said central aperture thereof to thereby block exterior access to said microporous membrane means, and
an aqueous solution of said analgesic and anti-inflammatory agents in said medication holding container in a concentration sufficient to provide a sustained analgesic/anti-inflammatory action.

12. A medication application system in accord with claim 11 wherein said analgesic/anti-inflammatory agent solution comprises a 3½% aqueous saline solution with aspirin in a concentration of between 0.15% and 2%.

13. A medication application system in accord with claim 11 wherein said analgesic/anti-inflammatory agent solution comprises a 3½% aqueous saline solution with aspirin in a concentration of substantially 136.3 mg per 100 ml.

14. A medication application system in accord with claim 11 wherein said analgesic/anti-inflammatory agent solution comprises an aqueous saline solution of between 0.02% and 3½% with acetaminophen in a concentration of between 0.05% and 20%.

15. A medication application system in accord with claim 11 wherein said analgesic/anti-inflammatory agent solution comprises an aqueous saline solution of between 0.02% and 20% with aspirin in a concentration of between 0.5% and 10% and acetaminophen in a concentration of between 0.05% and 10%.

16. A medication application system in accord with claim 11 wherein said analgesic/anti-inflammatory agent comprises an aqueous saline solution in a concentration of between 0.02% and 20% with Sulindac in a concentration between 0.01% and 0.20%.

17. In a medication application system for the sustained administration of a pharmacological preparation through an area of unbroken skin from a medciation contained in contact with the skin, the improvement in said container comprising
medication impermeable housing means forming a generally concave cavity open on one side and having flange means extending radially outward from the periphery of said cavity opening and integral with said housing means, said flange means having an annular depression therein on the side of said flange means nearest said concave cavity opening,
medication permeable micro-porous membrane means secured in said annular depression of said flange means and covering the open side of said cavity to thereby form a medication holding container permeable on one side only to the passage of medication, and
means secured to said housing means for adhering said medication holding container to the skin of a patient.

18. The medication application system of claim 17 further comprising a pharmaceutically effective amount of medication in said container.

19. The medication application system of claim 18 wherein said medication comprises a 3% aqueous sodium chloride solution with 1.6% glycerin containing 40 units of insulin per ml.

20. The medication application system of claim 18 wherein said medication comprises a 3½% aqueous sodium chloride solution with nitroglycerin between 12.5 mg and 37.5 mg per ml.

21. The medication application system of claim 18 wherein said medication comprises 0.5 mg of digitalis in 2 cc of a solution of 40% propylene glycol, 10% alcohol and water.

22. The medication application system of claim 18 wherein said medication comprises a sterile water solution containing 50 mg per ml quinidine gluconate.

23. The medication application system of claim 18 wherein said medication comprises a 3½% aqueous sodium chloride solution containing 4 mg per ml of Hydrocortisone.

24. In a medication application system for the sustained administration of a pharmacological preparation through an area of unbroken skin from a medication container in contact with the skin, the improvement in said container comprising
medication impermeable housing means forming a generally concave cavity open on one side, said housing means further comprises filling aperture means centrally located in said concave cavity and flange means extending radially outward from the periphery of said cavity opening and integral with said housing means, said flange means having an annular depression therein,
medication permeable micro-porous membrane means secured in said annular depression and extending over said concave cavity to thereby form a medication holding container permeable on one side only to the passage of medication, and skin adhering means secured to said flange of said housing means on the side opposite said annular depression.

25. The medication application system of claim 24 further comprising retaining plug means inserted in said filling aperture means to sealingly close said filling aperture.

26. The medication application system of claim 24 wherein said housing means further comprises one or more reinforcing rib means integrally formed within said housing means and depending therefrom into said cavity for supporting said micro-porous membrane means.

27. The medication application system of claim 24 wherein said skin adhering means further comprises adhesive means for adhesively securing said skin adhering means to both the opposite surface of said flange means from the side with said annular depression and to the skin of a patient.

28. The medication application system of claim 27 further comprising retaining ring means mechanically secured to said housing means to thereby compress and secure said skin adhering means to said flange means, said retaining ring means further comprising coding indicia applied thereto.

29. The medication application system of claim 28 comprising release sheet means secured to said skin adhering means radially outward from said flange means, said release sheet means having a central aperture therein equal to or larger in diameter than the flange diameter of said housing means and located concentric therewith.

30. The medication application system of claim 29 further comprising vapor barrier means sealingly adhered to said release sheet means and extending over said central aperture of said release sheet means to thereby block exterior access to said micro-porous membrane means.

31. In a medication application system for the sustained administration of a pharmaceutically effective amount of a medication through an area of unbroken skin from a medication container in contact with the skin, the improvement in said container comprising medication impermeable housing means forming a generally concave shaped cavity open on one side, flange means extending radially outward from the periphery of said cavity opening including an annular depression therein, filling aperture means centrally located in said concave cavity and reinforcing rib means integrally formed within said housing and depending therefrom into said concave cavity, medication permeable micro-porous membrane means secured to said annular depression and covering the open side of said cavity, retaining plug means sealingly inserted in said filling aperture means, skin adhering means having a central aperture whose diameter is substantially equal to that of said cavity opening and concentric therewith, said skin adhering means being secured to said housing's flange means on the side opposite said membrane means and comprising a plurality of holes perforated in said skin adhering means in the area thereof extending radially outward from said housing flange area, release sheet means having a central aperture equal to or larger in diameter than the inside flange diameter of said housing means and located concentric therewith, said release sheet means being adhesively secured to said skin adhering means, retaining ring means mechanically secured to said housing means to thereby compress and secure said skin adhering means to said housing flange means, and vapor barrier means sealingly adhered to said release sheet means and extending over said central aperture thereof to thereby block exterior access to said micro-porous membrane means.

* * * * *